US00RE46363E

(19) United States
(12) Reissued Patent
Moeller et al.

(10) Patent Number: US RE46,363 E
(45) Date of Reissued Patent: Apr. 11, 2017

(54) DIAL-DOWN MECHANISM FOR WIND-UP PEN

(71) Applicant: Novo Nordisk A/S, Bagsvaerd (DK)

(72) Inventors: Claus Schmidt Moeller, Fredensborg (DK); Christian Peter Enggaard, Vejby (DK); Bo Radmer, Hilleroed (DK); Tom Hede Markussen, Bagsvaerd (DK)

(73) Assignee: Novo Nordisk A/S, Bagsvaerd (DK)

(21) Appl. No.: 14/091,774

(22) Filed: Nov. 27, 2013

Related U.S. Patent Documents

Reissue of:
(64) Patent No.: 7,686,786
Issued: Mar. 30, 2010
Appl. No.: 11/665,486
PCT Filed: Oct. 20, 2005
PCT No.: PCT/EP2005/011285
§ 371 (c)(1),
(2) Date: Oct. 11, 2007
PCT Pub. No.: WO2006/045526
PCT Pub. Date: May 4, 2006

U.S. Applications:
(62) Division of application No. 13/431,019, filed on Mar. 27, 2012, which is an application for the reissue of Pat. No. 7,686,786.

(Continued)

(30) Foreign Application Priority Data

Oct. 21, 2004 (EP) ..... 04077900

(51) Int. Cl.
*A61M 5/20* (2006.01)
*A61M 5/145* (2006.01)
*A61M 5/315* (2006.01)

(52) U.S. Cl.
CPC ..... *A61M 5/14566* (2013.01); *A61M 5/3155* (2013.01); *A61M 5/31583* (2013.01);
(Continued)

(58) Field of Classification Search
CPC ..... A61M 5/14566; A61M 5/3155; A61M 5/31583; A61M 5/20; A61M 5/31535;
(Continued)

(56) References Cited

U.S. PATENT DOCUMENTS 854,390 A 5/1907 Bridge
2,392,196 A 1/1946 Smith
(Continued)

FOREIGN PATENT DOCUMENTS

AU 595723 1/1988
AU 2003232576 A1 1/2004
(Continued)

OTHER PUBLICATIONS

Annersten, M. et al., Insulin Pens Dribble From the Tip of the Needle After Injection, Practical Diabetes Int., vol. 17(4), pp. 109-111 (2000).

(Continued)

*Primary Examiner* — William Doerrler
(74) *Attorney, Agent, or Firm* — Wesley Nicolas

(57) ABSTRACT

The present invention relates to a dial-down mechanism for an injection device comprising a torsion spring for assisting injection of a dose of medicament from the injection device, the dial-down mechanism comprising dial-up cam arranged to receive and engage with a dial-up key, wherein the dial-up cam and the dial-up key are adapted to, upon rotation of a dose setting member in a first direction, cooperate to strain the torsion spring of the injection device, and a dial-down cam arranged to receive and engage with a dial-down key, wherein the dial-down cam and the dial-down key are (Continued)

Amended

Amended adapted to, upon rotation of the dose setting member in a second direction, cooperate to release the torsion spring of the injection device, the second rotation direction being opposite to the first rotation direction.

11 Claims, 5 Drawing Sheets

Related U.S. Application Data

(60) Provisional application No. 60/626,270, filed on Nov. 9, 2004.

(52) U.S. Cl.
CPC ..... *A61M 5/20* (2013.01); *A61M 5/31535* (2013.01); *A61M 5/31553* (2013.01); *A61M 5/31586* (2013.01); *A61M 5/31593* (2013.01); *A61M 2005/202* (2013.01)

(58) Field of Classification Search
CPC ..... A61M 5/31586; A61M 5/31593; A61M 5/31553; A61M 2005/202
USPC ..... 604/134, 135, 136, 131, 132, 133
See application file for complete search history.

(56) References Cited

U.S. PATENT DOCUMENTS 2,956,563 A 10/1960 Sarnoff
3,110,310 A 11/1963 Cislak
3,115,135 A 12/1963 Sarnoff
3,144,178 A 8/1964 Sarnoff et al.
3,556,099 A 1/1971 Knight et al.
3,729,003 A 4/1973 Hurschman
3,880,162 A 4/1975 Simmons
3,944,843 A 3/1976 Vaz Martins
4,026,288 A 5/1977 Costa et al.
4,231,368 A 11/1980 Becker
4,275,727 A 6/1981 Keeri-Szanto
4,277,227 A 7/1981 Jenkins
4,298,000 A 11/1981 Thill et al.
4,300,554 A 11/1981 Hessberg et al.
4,313,439 A 2/1982 Babb et al.
4,314,556 A 2/1982 Ma
4,368,731 A 1/1983 Schramm
RE31,315 E 7/1983 Jenkins et al.
4,393,723 A 7/1983 Brand
4,430,079 A 2/1984 Thill et al.
4,465,478 A 8/1984 Sabelman et al.
4,470,317 A 9/1984 Sabloewski et al.
4,493,704 A 1/1985 Beard et al.
4,498,904 A 2/1985 Turner et al.
4,515,584 A 5/1985 Abe et al.
4,568,335 A 2/1986 Updike et al.
4,584,439 A 4/1986 Paddock
4,585,439 A 4/1986 Michel
4,634,431 A 1/1987 Whitney et al.
4,676,122 A 6/1987 Szabo et al.
4,749,109 A 6/1988 Kamen
4,812,724 A 3/1989 Langer et al.
4,833,379 A 5/1989 Kaibel et al.
4,838,860 A 6/1989 Groshong et al.
4,865,591 A 9/1989 Sams
4,871,351 A 10/1989 Feingold
4,883,472 A 11/1989 Michel
4,893,291 A 1/1990 Bick et al.
4,898,578 A 2/1990 Rubalcaba, Jr.
4,919,596 A 4/1990 Slate et al.
4,924,737 A 5/1990 Gummow
4,936,833 A 6/1990 Sams
4,950,246 A 8/1990 Muller
4,973,318 A 11/1990 Holm et al.
4,988,337 A 1/1991 Ito
4,994,033 A 2/1991 Shockey et al.
4,998,922 A 3/1991 Kuracina et al.
5,000,744 A 3/1991 Hoffman et al.
5,002,537 A 3/1991 Hoffman et al.
5,011,479 A 4/1991 Le et al.
5,064,098 A 11/1991 Hutter, III et al.
5,078,698 A 1/1992 Stiehl et al.
5,104,380 A 4/1992 Holman et al.
5,104,388 A 4/1992 Quackenbush
5,112,317 A 5/1992 Michel
5,113,869 A 5/1992 Nappholz et al.
5,114,406 A 5/1992 Gabriel et al.
5,122,317 A 6/1992 Chen et al.
5,135,485 A 8/1992 Cohen et al.
5,154,698 A 10/1992 Compagnucci et al.
5,163,904 A 11/1992 Lampropoulos et al.
5,176,646 A 1/1993 Kuroda
5,207,752 A 5/1993 Sorenson et al.
5,221,268 A 6/1993 Barton et al.
5,226,342 A 7/1993 Panin
5,226,895 A 7/1993 Harris
5,226,896 A 7/1993 Harris
5,244,461 A 9/1993 Derlien
5,244,465 A 9/1993 Michel
5,246,417 A 9/1993 Haak et al.
5,257,987 A 11/1993 Athayde et al.
5,271,527 A 12/1993 Haber et al.
5,279,585 A 1/1994 Balkwill
5,279,586 A 1/1994 Balkwill
5,281,198 A 1/1994 Haber et al.
5,284,480 A 2/1994 Porter et al.
5,292,976 A 3/1994 Dessau et al.
5,295,976 A 3/1994 Harris
5,304,152 A 4/1994 Sams
5,308,340 A 5/1994 Harris
5,314,412 A 5/1994 Rex
5,318,540 A 6/1994 Athayde et al.
5,320,609 A 6/1994 Haber et al.
5,331,954 A 7/1994 Rex et al.
5,368,572 A 11/1994 Shirota
5,370,629 A 12/1994 Michel et al.
5,378,233 A 1/1995 Haber et al.
5,383,856 A 1/1995 Bersin
5,383,865 A 1/1995 Michel
5,408,387 A 4/1995 Murase et al.
5,440,976 A 8/1995 Giuliano et al.
5,445,606 A 8/1995 Haak et al.
5,447,150 A 9/1995 Bacon
5,478,316 A 12/1995 Bitdinger et al.
5,480,387 A 1/1996 Gabriel et al.
5,492,534 A 2/1996 Athayde et al.
5,496,286 A 3/1996 Stiehl et al.
5,505,697 A 4/1996 McKinnon, Jr. et al.
5,505,704 A 4/1996 Pawelka et al.
5,514,097 A 5/1996 Knauer
5,536,249 A 7/1996 Castellano et al.
5,546,932 A 8/1996 Galli
5,549,575 A 8/1996 Giambattista et al.
5,573,729 A 11/1996 Belgardt et al.
5,582,598 A 12/1996 Chanoch
5,584,815 A 12/1996 Pawelka et al.
5,591,136 A 1/1997 Gabriel
5,593,390 A 1/1997 Castellano et al.
5,599,314 A 2/1997 Neill
5,611,783 A 3/1997 Mikkelsen
5,611,784 A 3/1997 Barresi et al.
5,626,566 A 5/1997 Petersen et al.
5,628,309 A 5/1997 Brown
5,637,095 A 6/1997 Nason et al.
5,645,052 A 7/1997 Kersey
5,662,612 A 9/1997 Niehoff
5,674,204 A 10/1997 Chanoch
5,679,111 A 10/1997 Hjertman et al.
5,681,285 A 10/1997 Ford et al.
5,685,864 A 11/1997 Shanley et al.
5,688,251 A 11/1997 Chanoch
5,709,662 A 1/1998 Olive et al.
5,716,990 A 2/1998 Bagshawe et al.
5,720,733 A 2/1998 Brown

(56) References Cited

U.S. PATENT DOCUMENTS 5,725,508 A 3/1998 Chanoch et al.
5,728,074 A 3/1998 Castellano et al.
5,728,559 A 3/1998 Nilsson et al.
5,741,211 A 4/1998 Renirie et al.
5,743,889 A 4/1998 Sams
5,755,692 A 5/1998 Manicom
5,782,633 A 7/1998 Muhlbauer
5,807,334 A 9/1998 Hodosh et al.
5,814,022 A 9/1998 Antanavich et al.
5,820,602 A 10/1998 Kovelman et al.
5,823,998 A 10/1998 Yamagata
5,827,232 A 10/1998 Chanoch et al.
5,830,194 A 11/1998 Anwar et al.
5,843,036 A 12/1998 Olive et al.
5,879,360 A 3/1999 Crankshaw
5,879,630 A 3/1999 Lescouzeres et al.
5,882,718 A 3/1999 Pommer et al.
5,898,028 A 4/1999 Jensen et al.
5,921,966 A 7/1999 Bendek et al.
5,928,201 A 7/1999 Poulsen et al.
5,933,671 A 8/1999 Stephany et al.
5,938,642 A 8/1999 Burroughs et al.
5,947,934 A 9/1999 Hansen et al.
5,951,530 A 9/1999 Steengaard et al.
5,954,689 A 9/1999 Poulsen
5,954,700 A 9/1999 Kovelman
5,957,889 A 9/1999 Poulsen et al.
5,961,496 A 10/1999 Nielsen et al.
5,971,963 A 10/1999 Choi
5,980,491 A 11/1999 Hansen
5,984,900 A 11/1999 Mikkelsen
5,989,221 A 11/1999 Hjertman
5,998,989 A 12/1999 Lohberg
6,003,736 A 12/1999 Ljunggren
6,004,297 A 12/1999 Steenfeldt-Jensen et al.
6,010,485 A 1/2000 Buch-Rasmussen et al.
6,019,745 A 2/2000 Gray
6,033,376 A 3/2000 Rockley
6,033,377 A 3/2000 Rasmussen et al.
6,036,675 A 3/2000 Thorne et al.
6,048,336 A 4/2000 Gabriel
6,074,372 A 6/2000 Hansen
6,083,197 A 7/2000 Umbaugh
6,086,567 A 7/2000 Kirchhofer et al.
6,096,010 A 8/2000 Walters et al.
6,110,148 A 8/2000 Brown et al.
6,110,149 A 8/2000 Klitgaard et al.
6,129,080 A 10/2000 Pitcher et al.
6,146,361 A 11/2000 DiBiasi et al.
6,159,161 A 12/2000 Hodosh
6,161,364 A 12/2000 Kolberg
6,193,698 B1 2/2001 Kirchhofer et al.
6,221,046 B1 4/2001 Burroughs et al.
6,221,053 B1 4/2001 Walters et al.
6,231,540 B1 5/2001 Smedegaard
6,235,004 B1 5/2001 Steenfeldt-Jensen et al.
6,245,046 B1 6/2001 Sibbitt
6,248,090 B1 6/2001 Jensen et al.
6,248,095 B1 6/2001 Giambattista et al.
6,258,062 B1 7/2001 Thielen et al.
6,268,722 B1 7/2001 Kogure et al.
6,269,340 B1 7/2001 Ford et al.
6,277,097 B1 8/2001 Mikkelsen et al.
6,277,098 B1 8/2001 Klitmose et al.
6,281,225 B1 8/2001 Hearst et al.
6,283,941 B1 9/2001 Schoenfeld et al.
6,287,283 B1 9/2001 Ljunggreen et al.
6,302,869 B1 10/2001 Klitgaard
6,312,413 B1 11/2001 Jensen et al.
6,340,357 B1 1/2002 Poulsen et al.
6,364,860 B1 4/2002 Steck et al.
6,379,339 B1 4/2002 Klitgaard et al.
6,383,167 B2 5/2002 Kirchhofer et al.
6,391,005 B1 5/2002 Lum et al.
6,419,661 B1 7/2002 Kuhr et al.
6,514,230 B1 2/2003 Munk et al.
6,537,251 B2 3/2003 Klitmose
6,547,755 B1 4/2003 Lippe et al.
6,547,763 B2 4/2003 Steenfeldt-Jensen et al.
6,547,764 B2 4/2003 Larsen et al.
6,562,011 B1 5/2003 Buch-Rasmussen et al.
6,569,126 B1 5/2003 Poulsen et al.
6,582,404 B1 6/2003 Klitgaard et al.
6,585,698 B1 7/2003 Packman et al.
6,599,272 B1 7/2003 Hjertman et al.
6,605,067 B1 8/2003 Larsen
6,613,019 B2 9/2003 Munk
6,663,602 B2 12/2003 Moller
6,666,849 B1 12/2003 Marshall et al.
6,673,033 B1 1/2004 Sciulli et al.
6,692,472 B2 2/2004 Hansen et al.
6,699,224 B2 3/2004 Kirchhofer et al.
6,716,198 B2 4/2004 Larsen
6,726,661 B2 4/2004 Munk et al.
6,752,798 B2 6/2004 McWethy et al.
6,770,288 B2 8/2004 Duirs
6,796,970 B1 9/2004 Klitmose et al.
6,852,404 B2 2/2005 Kuwajima et al.
6,887,238 B2 5/2005 Jahns et al.
6,893,415 B2 5/2005 Madsen et al.
6,899,698 B2 5/2005 Sams
6,899,699 B2 5/2005 Enggaard
6,945,961 B2 9/2005 Miller et al.
7,008,399 B2 3/2006 Larsen et al.
7,080,936 B1 7/2006 Simpson
7,090,662 B2 8/2006 Wimpenny et al.
7,094,221 B2 8/2006 Veasey et al.
7,104,972 B2 9/2006 Moller et al.
7,133,329 B2 11/2006 Skyggebjerg et al.
7,175,055 B2 2/2007 Hansen et al.
7,195,609 B2 3/2007 Huegli
7,195,616 B2 3/2007 Diller et al.
7,241,278 B2 7/2007 Moller
7,500,966 B2 3/2009 Hommann
7,678,084 B2 3/2010 Judson et al.
7,686,786 B2 3/2010 Moller et al.
7,704,238 B2 4/2010 Diller et al.
7,771,399 B2 8/2010 Burren et al.
8,048,037 B2 11/2011 Kohlbrenner et al.
8,202,256 B2 6/2012 Moller
8,206,361 B2 6/2012 Moller
8,267,899 B2 9/2012 Moller
8,870,831 B2 10/2014 Holmqvist et al.
9,132,239 B2 9/2015 Moller et al.
2001/0016571 A1 8/2001 Ohkubo et al.
2001/0034506 A1 10/2001 Hirschman et al.
2001/0053893 A1 12/2001 Larsen
2002/0002326 A1 1/2002 Causey et al.
2002/0002354 A1 1/2002 Vetter et al.
2002/0007154 A1 1/2002 Hansen et al.
2002/0020654 A1 2/2002 Eilersen
2002/0049415 A1 4/2002 Fukuda
2002/0052578 A1 5/2002 Moller
2002/0077852 A1 6/2002 Ford et al.
2002/0107486 A1 8/2002 Munk
2002/0120235 A1 8/2002 Enggaard
2002/0165500 A1 11/2002 Bechtold et al.
2002/0173752 A1* 11/2002 Polzin ..... 604/233
2002/0188250 A1 12/2002 Landau et al.
2003/0009133 A1 1/2003 Ramey
2003/0039679 A1 2/2003 Duirs
2003/0040715 A1 2/2003 D'Antonio et al.
2003/0050609 A1 3/2003 Sams
2003/0073954 A1 4/2003 Moberg et al.
2003/0114800 A1 6/2003 Veasey et al.
2003/0172924 A1 9/2003 Staniforth et al.
2003/0176871 A1 9/2003 Pavlov et al.
2003/0216663 A1 11/2003 Jersey-Willuhn et al.
2003/0233075 A1 12/2003 Huegli
2004/0010204 A1 1/2004 Weber et al.
2004/0024361 A1 2/2004 Fago et al.
2004/0051368 A1 3/2004 Caputo et al.
2004/0054326 A1 3/2004 Hommann et al.
2004/0059299 A1 3/2004 Moller

(56) References Cited

U.S. PATENT DOCUMENTS

| | | | |
|---|---|---|---|
| 2004/0097879 | A1 | 5/2004 | Woolston |
| 2004/0108339 | A1 | 6/2004 | Hansen et al. |
| 2004/0158304 | A1 | 8/2004 | Cory et al. |
| 2004/0171983 | A1 | 9/2004 | Sparks et al. |
| 2004/0186431 | A1 | 9/2004 | Graf et al. |
| 2004/0199117 | A1 | 10/2004 | Giambattista et al. |
| 2004/0207385 | A1 | 10/2004 | Gafner et al. |
| 2004/0210199 | A1 | 10/2004 | Atterbury et al. |
| 2004/0230157 | A1 | 11/2004 | Perry et al. |
| 2004/0236282 | A1 | 11/2004 | Braithwaite |
| 2004/0249348 | A1 | 12/2004 | Wimpenny et al. |
| 2004/0260247 | A1 | 12/2004 | Veasey et al. |
| 2004/0267207 | A1 | 12/2004 | Veasey et al. |
| 2004/0267208 | A1 | 12/2004 | Veasey et al. |
| 2005/0004529 | A1 | 1/2005 | Veasey et al. |
| 2005/0019400 | A1 | 1/2005 | Deveney et al. |
| 2005/0033244 | A1 | 2/2005 | Veasey et al. |
| 2005/0055011 | A1 | 3/2005 | Enggaard |
| 2005/0090782 | A1* | 4/2005 | Marshall et al. ..... 604/211 |
| 2005/0197625 | A1 | 9/2005 | Haueter et al. |
| 2005/0205083 | A1 | 9/2005 | Staniforth et al. |
| 2005/0209570 | A1 | 9/2005 | Moller |
| 2005/0268915 | A1 | 12/2005 | Wassenaar et al. |
| 2006/0118612 | A1 | 6/2006 | Christoffersen et al. |
| 2006/0258988 | A1 | 11/2006 | Keitel et al. |
| 2006/0264838 | A1 | 11/2006 | Volckmann et al. |
| 2007/0093761 | A1 | 4/2007 | Veasey et al. |
| 2007/0167916 | A1 | 7/2007 | Lee et al. |
| 2007/0244445 | A1 | 10/2007 | Moller |
| 2007/0265568 | A1 | 11/2007 | Tsals et al. |
| 2008/0065026 | A1 | 3/2008 | Moller |
| 2008/0147005 | A1 | 6/2008 | Moller et al. |
| 2008/0221530 | A1 | 9/2008 | Glejbol et al. |
| 2008/0281275 | A1 | 11/2008 | Moller |
| 2008/0306445 | A1 | 12/2008 | Burren et al. |
| 2008/0312592 | A1 | 12/2008 | Barrow-Williams et al. |
| 2009/0043264 | A1 | 2/2009 | Glejbol et al. |
| 2009/0062748 | A1 | 3/2009 | Moller et al. |
| 2009/0209920 | A1 | 8/2009 | Moller et al. |
| 2011/0046565 | A1 | 2/2011 | Radmer et al. |
| 2011/0125100 | A1 | 5/2011 | Schwirtz et al. |
| 2012/0095410 | A1 | 4/2012 | Moller et al. |
| 2012/0209208 | A1 | 8/2012 | Stefanski |
| 2013/0204197 | A1 | 8/2013 | Bicknell et al. |
| 2013/0274676 | A1 | 10/2013 | Ekman et al. |
| 2013/0310739 | A1 | 11/2013 | Galbraith et al. |
| 2014/0350478 | A1 | 11/2014 | Hansen et al. |
| 2015/0148750 | A1 | 5/2015 | Pedersen et al. |

FOREIGN PATENT DOCUMENTS

| | | | |
|---|---|---|---|
| BR | PI0613926 | A2 | 2/2011 |
| CA | 2359375 | A1 | 7/2000 |
| CN | 1214292 | A | 4/1999 |
| DE | 3048135 | A1 | 7/1982 |
| DE | 3236374 | A1 | 4/1984 |
| DE | 3609555 | A1 | 9/1987 |
| DE | 3638984 | A1 | 5/1988 |
| DE | 3923079 | A1 | 1/1991 |
| DE | 4223958 | A1 | 1/1993 |
| DE | 4419235 | A1 | 12/1995 |
| DE | 19503230 | A1 | 8/1996 |
| DE | 29513214 | U1 | 1/1997 |
| DE | 19723647 | C1 | 12/1998 |
| DE | 19838760 | A1 | 4/2000 |
| DE | 29907880 | U1 | 9/2000 |
| DE | 10103287 | A1 | 8/2001 |
| DE | 20209051 | U1 | 4/2003 |
| DE | 10201875 | C1 | 5/2003 |
| DE | 10229122 | A1 | 2/2004 |
| DE | 10237258 | A1 | 3/2004 |
| DE | 20317377 | U1 | 4/2005 |
| DE | 102004046003 | A1 | 3/2006 |
| DK | 200100240 | | 11/2001 |
| DK | 2005/00116 | U1 | 6/2005 |
| EA | 008160 | | 4/2007 |
| EP | 15617 | | 9/1980 |
| EP | 017318 | A1 | 10/1980 |
| EP | 0064858 | A1 | 11/1982 |
| EP | 295075 | | 12/1988 |
| EP | 327810 | A2 | 8/1989 |
| EP | 327910 | | 8/1989 |
| EP | 338806 | | 10/1989 |
| EP | 0362484 | A2 | 4/1990 |
| EP | 387854 | | 9/1990 |
| EP | 422482 | | 4/1991 |
| EP | 454331 | | 10/1991 |
| EP | 498737 | | 8/1992 |
| EP | 879610 | | 8/1992 |
| EP | 608343 | | 4/1993 |
| EP | 554995 | A1 | 8/1993 |
| EP | 554996 | | 8/1993 |
| EP | 594349 | | 4/1994 |
| EP | 615762 | | 9/1994 |
| EP | 0615762 | A1 | 9/1994 |
| EP | 513128 | | 7/1995 |
| EP | 0673482 | | 9/1995 |
| EP | 679440 | A1 | 11/1995 |
| EP | 702970 | | 3/1996 |
| EP | 0704225 | A2 | 4/1996 |
| EP | 0708179 | A2 | 4/1996 |
| EP | 897728 | | 2/1999 |
| EP | 897729 | A2 | 2/1999 |
| EP | 908273 | | 4/1999 |
| EP | 0937471 | | 8/1999 |
| EP | 0937472 | | 8/1999 |
| EP | 937476 | | 8/1999 |
| EP | 0937476 | A2 | 8/1999 |
| EP | 1003581 | | 8/1999 |
| EP | 956873 | A2 | 11/1999 |
| EP | 1351732 | | 1/2001 |
| EP | 1074273 | | 2/2001 |
| EP | 1095668 | A1 | 5/2001 |
| EP | 1216717 | A1 | 6/2002 |
| EP | 1216719 | A1 | 6/2002 |
| EP | 1000631 | | 7/2002 |
| EP | 0747391 | | 3/2004 |
| EP | 1462134 | A1 | 9/2004 |
| EP | 1541185 | | 6/2005 |
| EP | 1557163 | | 7/2005 |
| EP | 1557189 | A1 | 7/2005 |
| EP | 1568389 | | 8/2005 |
| EP | 1304129 | | 11/2005 |
| EP | 1610848 | A1 | 1/2006 |
| EP | 1645301 | | 4/2006 |
| EP | 1723977 | | 11/2006 |
| EP | 1728529 | | 12/2006 |
| EP | 1768725 | A1 | 4/2007 |
| EP | 1782853 | | 5/2007 |
| EP | 1819382 | | 8/2007 |
| EP | 1909871 | A1 | 4/2008 |
| EP | 1926514 | A1 | 6/2008 |
| EP | 2000161 | | 12/2008 |
| EP | 2019701 | A1 | 2/2009 |
| EP | 2373361 | A1 | 10/2011 |
| FR | 2583291 | | 12/1986 |
| FR | 2622457 | | 5/1989 |
| FR | 2697434 | A1 | 5/1994 |
| FR | 2740345 | | 4/1997 |
| FR | 2767479 | | 2/1999 |
| FR | 2857654 | | 1/2005 |
| GB | 574705 | | 1/1946 |
| GB | 664044 | | 1/1952 |
| GB | 2091107 | | 7/1982 |
| GB | 2153445 | | 8/1985 |
| GB | 2229497 | | 9/1990 |
| GB | 2309644 | | 8/1997 |
| GB | 0007071.4 | | 3/2000 |
| IN | 165367 | | 3/1986 |
| JP | 56-163486 | | 12/1981 |
| JP | 57-000033 | | 1/1982 |
| JP | 01-035671 | A | 2/1989 |
| JP | 01-100495 | | 4/1989 |
| JP | 02071758 | A | 3/1990 |

(56) References Cited

FOREIGN PATENT DOCUMENTS

| | | | |
|---|---|---|---|
| JP | 02-126184 | | 5/1990 |
| JP | 02-182267 | | 7/1990 |
| JP | 4-224764 | | 8/1992 |
| JP | 04256757 | A | 9/1992 |
| JP | 4-507059 | | 12/1992 |
| JP | 05-337179 | | 12/1993 |
| JP | 06-055644 | | 1/1994 |
| JP | 06-034825 | | 10/1994 |
| JP | 06-296691 | | 10/1994 |
| JP | H07-500039 | | 1/1995 |
| JP | 7-502678 | | 3/1995 |
| JP | 09166474 | | 6/1997 |
| JP | 11511364 | | 10/1999 |
| JP | 3017167 | | 11/1999 |
| JP | 2000237308 | | 9/2000 |
| JP | 2002503122 | | 1/2002 |
| JP | 2003284777 | | 10/2003 |
| JP | 2004503303 | A | 2/2004 |
| JP | 2004-516895 | | 6/2004 |
| JP | 2004533285 | A | 11/2004 |
| JP | 2005536300 | A | 12/2005 |
| JP | 2006250582 | | 9/2006 |
| JP | 2007-509662 | | 4/2007 |
| JP | 2008-528071 | A | 7/2008 |
| JP | 2008-196696 | A | 8/2008 |
| JP | 2010523183 | A | 7/2010 |
| JP | 2011524212 | A | 9/2011 |
| PL | EP 1804865 | | 10/2005 |
| PL | 208660 | B1 | 5/2011 |
| PL | EP 2373361 | | 9/2012 |
| RU | 2111019 | | 5/1997 |
| RU | 2091087 | | 9/1997 |
| RU | 2212254 | | 9/2003 |
| RU | 2254878 | C2 | 6/2005 |
| SU | 1528330 | A3 | 12/1989 |
| WO | 8502256 | | 5/1985 |
| WO | 8702895 | A1 | 5/1987 |
| WO | 8907463 | | 8/1989 |
| WO | 90/09202 | | 8/1990 |
| WO | 9110460 | A1 | 7/1991 |
| WO | 9110677 | | 7/1991 |
| WO | 91/14467 | A1 | 10/1991 |
| WO | 9301573 | | 1/1993 |
| WO | 9303780 | | 3/1993 |
| WO | 9307922 | | 4/1993 |
| WO | 9412228 | | 6/1994 |
| WO | 95/21645 | A1 | 8/1995 |
| WO | 9524233 | | 9/1995 |
| WO | 9607443 | | 3/1996 |
| WO | 9626754 | | 9/1996 |
| WO | 96/32973 | | 10/1996 |
| WO | 9638190 | | 12/1996 |
| WO | 9707841 | | 3/1997 |
| WO | 9710865 | A1 | 3/1997 |
| WO | 9730742 | | 8/1997 |
| WO | 9733638 | | 9/1997 |
| WO | 9734919 | | 9/1997 |
| WO | 9736626 | | 10/1997 |
| WO | 9810813 | | 3/1998 |
| WO | 9856436 | | 12/1998 |
| WO | 9856439 | | 12/1998 |
| WO | 9857688 | | 12/1998 |
| WO | 9907425 | | 2/1999 |
| WO | 9915214 | | 4/1999 |
| WO | 9916487 | | 4/1999 |
| WO | 9921598 | | 5/1999 |
| WO | 9938554 | | 8/1999 |
| WO | 9948546 | | 9/1999 |
| WO | 9965548 | A1 | 12/1999 |
| WO | 0015224 | A1 | 3/2000 |
| WO | 0037098 | A1 | 6/2000 |
| WO | 0037129 | | 6/2000 |
| WO | 00/51668 | | 9/2000 |
| WO | 01/10484 | | 2/2001 |
| WO | 01/19434 | A1 | 3/2001 |
| WO | 0126710 | | 4/2001 |
| WO | 01/30425 | | 5/2001 |
| WO | 0172361 | | 10/2001 |
| WO | 0195959 | A1 | 12/2001 |
| WO | 0205876 | | 1/2002 |
| WO | 0224257 | | 3/2002 |
| WO | 02/050214 | A2 | 6/2002 |
| WO | 02/053214 | | 7/2002 |
| WO | WO 02/053214 | A1 | 7/2002 |
| WO | 02064196 | | 8/2002 |
| WO | 02/076535 | | 10/2002 |
| WO | 02/076537 | | 10/2002 |
| WO | 02076536 | | 10/2002 |
| WO | 02/092153 | A2 | 11/2002 |
| WO | 03/057285 | A2 | 7/2003 |
| WO | 03/057286 | A1 | 7/2003 |
| WO | 03057283 | | 7/2003 |
| WO | 03063680 | | 8/2003 |
| WO | 03080160 | | 10/2003 |
| WO | 03099357 | | 12/2003 |
| WO | 2004/002556 | A1 | 1/2004 |
| WO | 2004004825 | | 1/2004 |
| WO | 2004007002 | A1 | 1/2004 |
| WO | 2004/024218 | | 3/2004 |
| WO | 2004/028598 | A1 | 4/2004 |
| WO | 2006/045529 | | 4/2004 |
| WO | 2004035113 | A2 | 4/2004 |
| WO | 2004054644 | A1 | 7/2004 |
| WO | 2004/078240 | | 9/2004 |
| WO | 2004/078242 | A2 | 9/2004 |
| WO | 2004078239 | A1 | 9/2004 |
| WO | 2004078241 | | 9/2004 |
| WO | 2004080306 | | 9/2004 |
| WO | 2004084795 | | 10/2004 |
| WO | 2004/093940 | A2 | 11/2004 |
| WO | 2004095379 | | 11/2004 |
| WO | 2005018721 | | 3/2005 |
| WO | 2005037352 | | 4/2005 |
| WO | 2005/046770 | | 5/2005 |
| WO | 2005089835 | | 9/2005 |
| WO | 2005097233 | | 10/2005 |
| WO | 2005097240 | | 10/2005 |
| WO | 2005/102421 | A1 | 11/2005 |
| WO | 2006/003130 | A1 | 1/2006 |
| WO | 2006/026754 | A2 | 3/2006 |
| WO | 2006/037434 | A1 | 4/2006 |
| WO | 2006039930 | A1 | 4/2006 |
| WO | 2006040296 | A2 | 4/2006 |
| WO | 2006/045528 | | 5/2006 |
| WO | 2006045425 | | 5/2006 |
| WO | 2006045525 | | 5/2006 |
| WO | 2006045526 | A1 | 5/2006 |
| WO | 2006/069454 | | 7/2006 |
| WO | 2006076921 | | 7/2006 |
| WO | 2006116997 | | 11/2006 |
| WO | 2006/128794 | | 12/2006 |
| WO | 2007021195 | A1 | 2/2007 |
| WO | 2007/030957 | | 3/2007 |
| WO | 2007041843 | | 4/2007 |
| WO | 2007063342 | A1 | 6/2007 |
| WO | 2007104636 | A1 | 9/2007 |
| WO | 2007107558 | A2 | 9/2007 |
| WO | 2007107561 | | 9/2007 |
| WO | 2007/134954 | | 11/2007 |
| WO | 2008/003130 | A1 | 1/2008 |
| WO | 2008/031239 | A1 | 3/2008 |
| WO | 2008/037801 | | 4/2008 |
| WO | 2008057223 | | 5/2008 |
| WO | 2010046394 | A1 | 4/2010 |
| WO | 2010089418 | A2 | 8/2010 |
| WO | 2011025448 | A1 | 3/2011 |
| WO | 2011136718 | A1 | 11/2011 |
| WO | 2013/178372 | A1 | 12/2013 |

OTHER PUBLICATIONS

Answer in *Novo Nordisk A/S* v. *Sanofi-Aventis U.S. LLC and Sanofi-Aventis* downloaded from Pacer on Feb. 29, 2008.

(56) References Cited

OTHER PUBLICATIONS

Beckmann, Sensors, Memory, Circuits, Polyapply Newsletter, vol. 1(3), (2006).
Chia Kai Su et al, Process Biochemistry, 2006, vol. 41, Part 2, pp. 257-263.
Common Insulin Injection Challenges: http://www.bd.com/us/diabetes/page.aspx?cat=7001&id=7265.
Complaint in *Novo Nordisk A/S* v. *Sanofi-Aventis U.S. LLC and Sanofi-Aventis* downloaded from Pacer on Feb. 29, 2008.
Declaration of Benard Sams in *Novo Nordisk A/S* v. *Sanofi-Aventis U.S. LLC and Sanofi-Aventis* downloaded from Pacer on Feb. 29, 2008.
Dennison, Clive et al, Protein Expression and Purification, 1997, vol. 11, Part 2, pp. 149-161.
Fransson et al, Pharmaceutical Research, 1997, vol. 14, Part 5, pp. 606-612.
Gnanalingham, M.G. et al., Accuracy and Reproducibility of Low Dose Insulin Administration Using Pen-Injectors and Syringes, Downloaded From adc.bmj.com on Jan. 9, 2008.
International Search Report and Written Opinion issued in connection with counterpart PCT Application No. PCT/EP2006/061747, mailed Sep. 29, 2006.
Leonil et al, Enzyme and Microbiol Technology, 1994, vol. 16, Part 7, pp. 591-595.
Owen Mumford Product Range.
File history of U.S. Appl. No. 10/610,926 which is owned by the same assignee as U.S. Appl. No. 11/122,289 and U.S. Appl. No. 11/765,789.
Paule, B.J.A. et al, Protein Expression and Purification, 2004, vol. 34, Part 2, pp. 311-316.
Search Report issued in connection with counterpart Danish Application No. PA 2005 00588, mailed Feb. 13, 2006.
Search Report issued in connection with counterpart Danish Application No. PA 2005 00589, mailed Feb. 16, 2006.
Search Report Issued in Connection With PCT Appln. No. PCT/EP2007/052630, Mailed Nov. 12, 2007.
Search Report issued in connection with European Application No. 06005599.3, mailed Oct. 4, 2006.
Search Report issued in connection with PCT Application No. PCT/EP2007/052633, mailed Feb. 20, 2008.
Search Report Issued in Connection With European Appln No. 06005602.5, Mailed Oct. 16, 2006.
Trankler, Hans-Rolf, R. Oldenbourg, Verlag, Munchen, Wien, Taschenbuch Der Messtechnik, 1996.
Reissue U.S. Appl. No. 10/442,855 File History.
Reissue U.S. Appl. No. 10/960,900 File History.
Reissue U.S. Appl. No. 11/121,331 File History.
Reissue U.S. Appl. No. 11/640,610 File History.
May 17, 2002 Office Action in U.S. Appl. No. 09/768,760 and accompanying 892 and 1149 forms.
File history of U.S. Appl. No. 10/610,926, which is owned by the same assignee as U.S. Appl. No. 11/765,789.
Advisory Action mailed on Mar. 23, 2010 in U.S. Appl. No. 11/122,289 filed on May 4, 2005 by Moller et al.
Notice of Opposition by Owen Mumford (UK).
Notice of Opposition by Genentech (USA).
Notice of Opposition by Techpharma (CH) Including English Translation.
Opposition in Related European Patent Application EP 02711784.5 of Sep. 19, 2008.
Validity Opinion by the UK PTO.
Opinion of US District Court for the District of NJ in *Novo Nordisk A/S* v. *Sanofi-Aventis U.S. LLC and Sanofi-Aventis* Denying motion of a preliminary injunction entered Feb. 20, 2008.
Written Opinion issued in connection with counterpart PCT Application No. PCT/EP2006/061747, mailed Nov. 8, 2006.
Written Opinion issued in connection with counterpart PCT Application No. PCT/EP2006/061748, mailed Nov. 8, 2006.
Rose, Keith et al., Bioconjugate Chemistry, "Natural Peptides as Building Blocks for the Synthesis of Large Protein-Like Molecules With Hydrazone and Oxime Linkages", 1996, vol. 7, 2, pp. 552-556.
Yurkovetskiy, A. et al., Biomacromolecules., "Fully Degradable Hydrophilic Polyals for Protein Modification", 2005, vol. 6, 5, pp. 2648-2658.
International Search Report and Written Opinion issued in connection with counterpart PCT Application No. PCT/EP2006/061748 mailed Aug. 10, 2006.

* cited by examiner

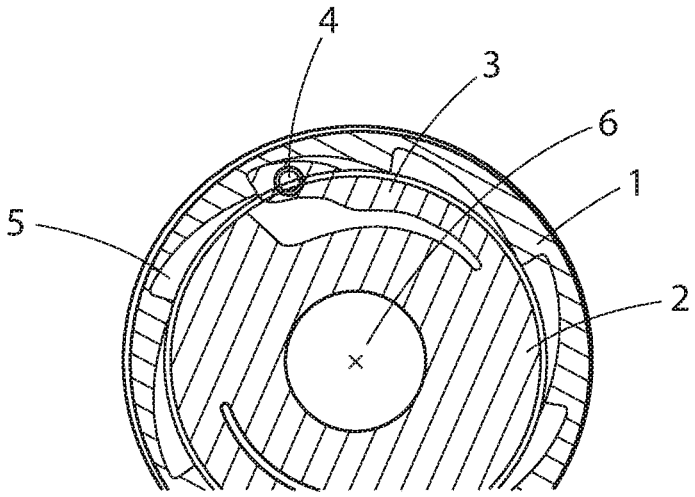
Fig. 1A Amended
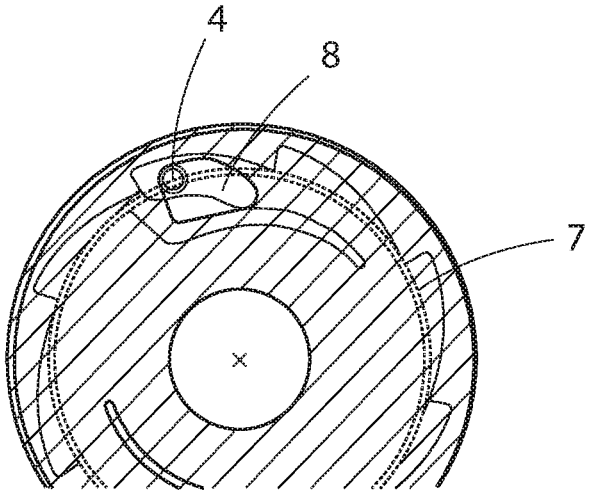
Fig. 1B Amended

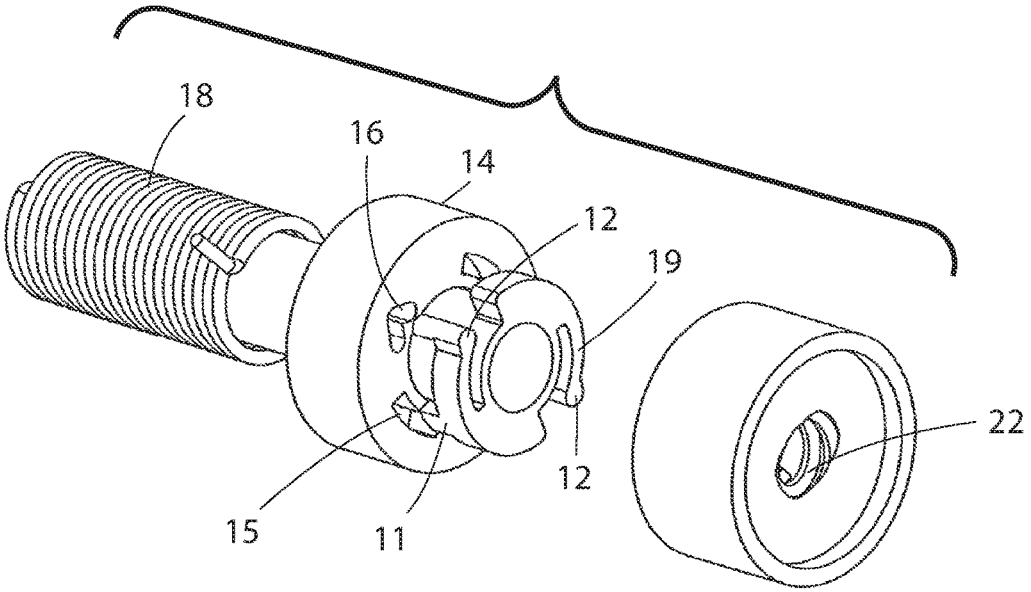
Fig. 2A Amended
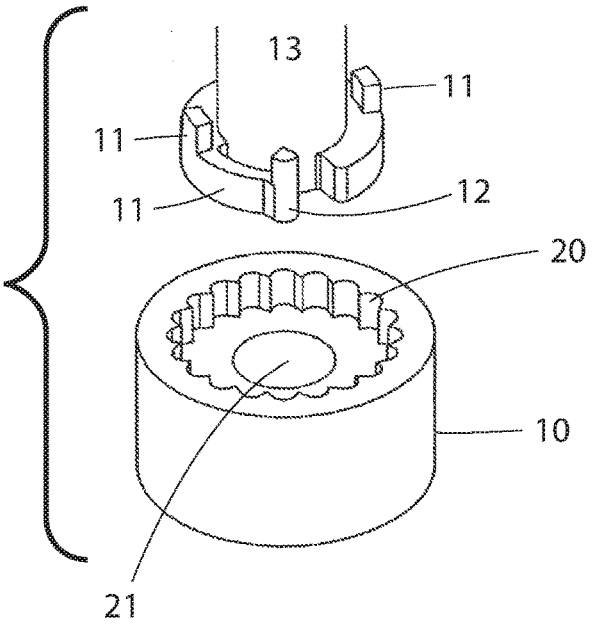
Fig. 2B Amended

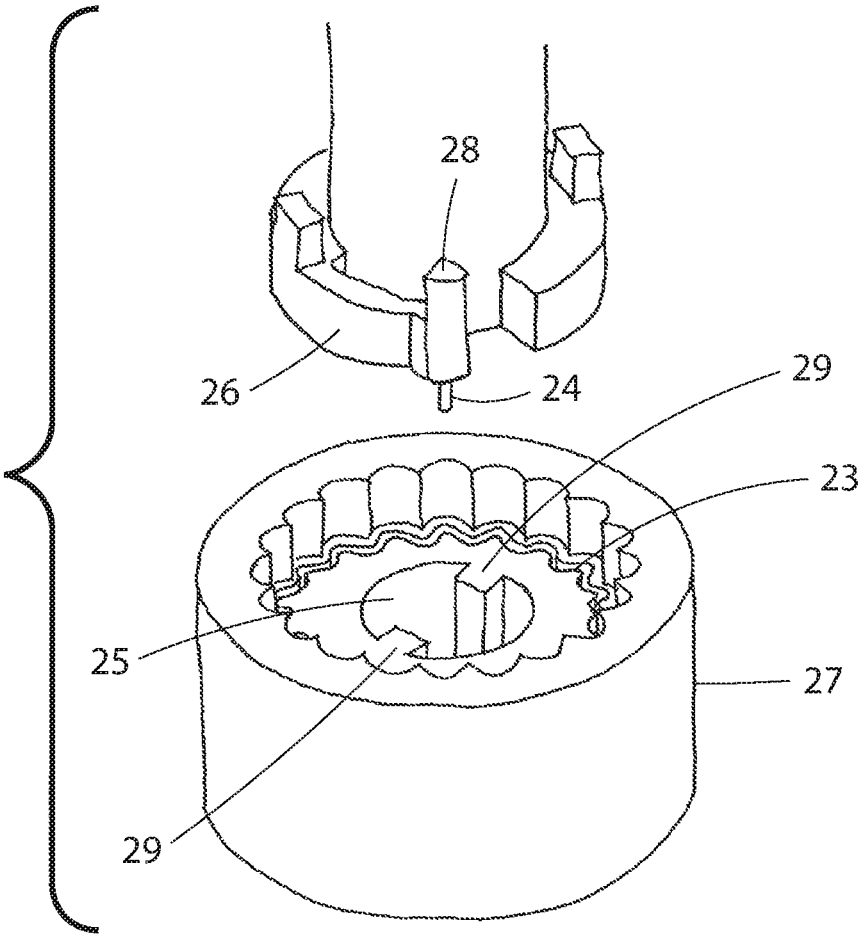
Fig. 3 Amended

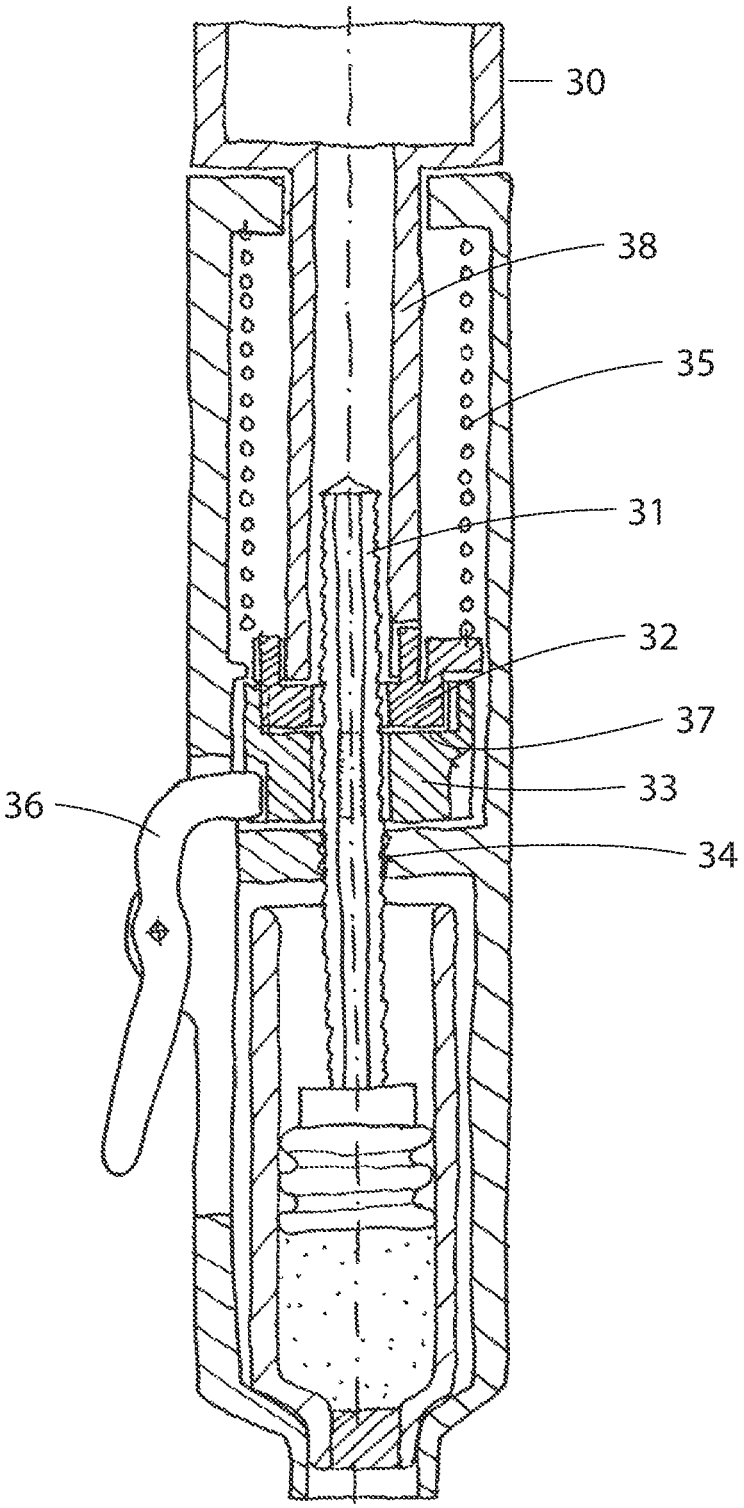
Fig. 4 Amended

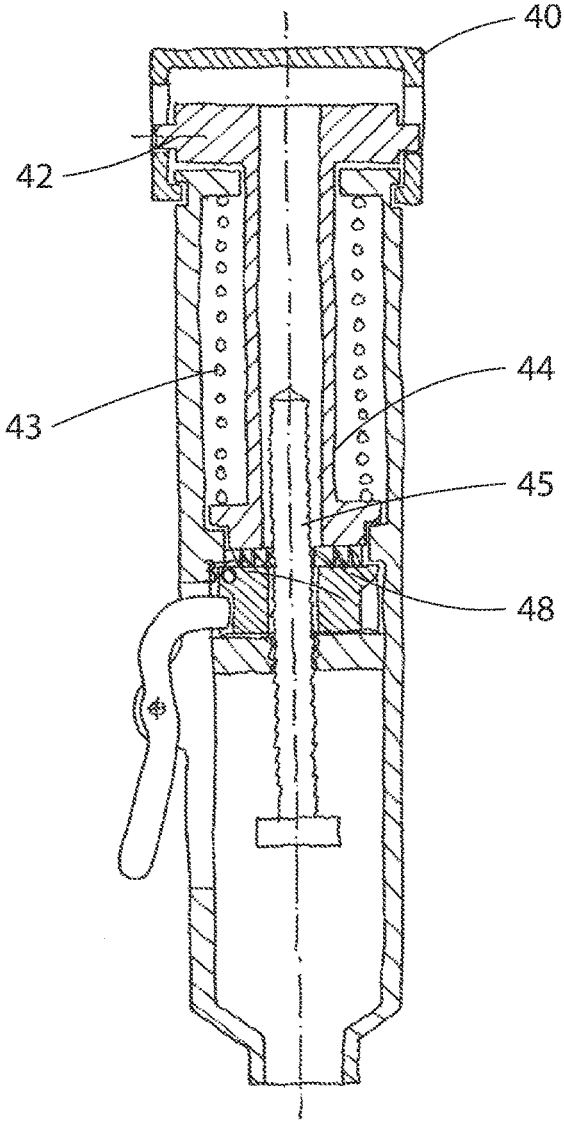
FIG. 5A Amended
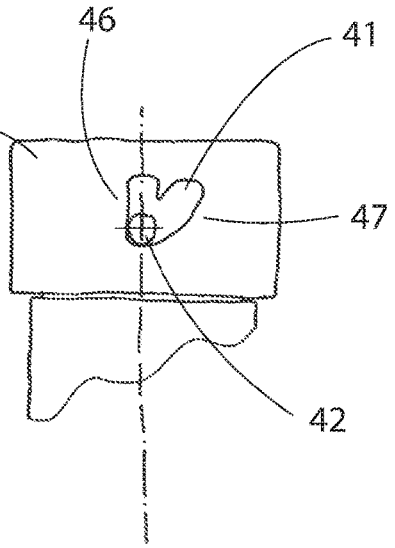
FIG. 5B Amended

DIAL-DOWN MECHANISM FOR WIND-UP PEN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This application is a 35 U.S.C. § 371 national stage application of International Patent Application PCT/EP2005/011285 (published as WO 2006/045526), filed Oct. 20, 2005, which claimed priority of European Patent Application 04077900.1, filed Oct. 21, 2004; this application further claims priority under 35 U.S.C. § 119 of U.S. Provisional Application 60/626,270, filed Nov. 9, 2004.] *This application is a Divisional Reissue of U.S. application Ser. No. 13/431,019, filed Mar. 27, 2012, which is an Application for Reissue of U.S. Pat. No. 7,686,786, issued Mar. 30, 2010 (U.S. application Ser. No. 11/665,486, filed Oct. 11, 2007), which is a 35 U.S.C. §371 national stage application of International Patent Application PCT/EP2005/011285 (published as WO2006/045526), filed Oct. 20, 2005, which claimed priority of European Patent Application 04077900.1, filed Oct. 21, 2004; this application further claims priority under 35 U.S.C. §119 of U.S. Provisional Application 60/626,270, filed Nov. 9, 2004, incorporated herein by reference.*

FIELD OF THE INVENTION

The present invention relates to a dial-down mechanism for automatic wind-up pens. In particular, the present invention relates to integrated axial and radial dial-down mechanisms for wind-up pens.

BACKGROUND OF THE INVENTION

In known injection devices, such as wind-up pens, based on torsion springs, the use of dial-down mechanisms rely on that the user of the injection device applies a force to a rotatable dose setting member of the injection device. The force must be applied in order to axially withdraw the dose setting member a certain distance to release the dose setting member from a toothing mechanism or ratchet positioned within the body of the injection device. By releasing the dose setting member from this toothing mechanism the dose setting member can be reversed by rotation and set at a new and lower dose.

An example of a known wind-up pen applying a torsion spring may for example be found in U.S. Pat. No. 5,104,380. However, the pen suggested in U.S. Pat. No. 5,104,380 does not offer a dial-down mechanism. A dial-down mechanism is provided in WO 02/053214. However, the proposed solution in WO 02/053214 involves a linear spring.

It is a disadvantage of known torsion spring-based dial-down systems that the user must apply a force to withdraw the dose setting member a certain axial distance and, at the same time, adjust the angular position of the dose setting member. Especially for persons having reduced motoric skills or reduced finger strength, such as children, elderly people or disabled people this is a rather complicated procedure.

US 2004/199117 discloses a medication delivery pen including an arrangement where incorrect dosage settings may be corrected by a user via a dial-back feature that enables the user to reset the dose amount without expelling medication and without having to dial a dose knob to an extended, reset position. The medication delivery pen of US 2004/199117 is a so-called manual pen where the injection of a medicament from the pen is driven by a force purely provided by the user of the pen. Thus, the injection of a medicament is not assisted by any resilient member, such as a spring, and the dial-down arrangement disclosed in US 2004/199117 is not arranged to maintain a resilient member in a given strained position.

It is an object of the present invention to provide a dial-down mechanism for automatic wind-up pens. Automatic wind-up pens are here to be understood as pens having a resilient member, such as a spring, to assist injecting a medicament from an injection device.

SUMMARY OF THE INVENTION

The above-mentioned object is complied with by providing, in a first aspect, a dial-down mechanism for an injection device comprising a torsion spring for assisting injection of a dose of medicament from the injection device, the dial-down mechanism comprising dial-up cam arranged to receive and engage with a dial-up key, wherein the dial-up cam and the dial-up key are adapted to, upon rotation of a dose setting member in a first direction, cooperate to strain the torsion spring of the injection device, and a dial-down cam arranged to receive and engage with a dial-down key, wherein the dial-down cam and the dial-down key are adapted to, upon rotation of the dose setting member in a second direction, cooperate to release the torsion spring of the injection device, the second rotation direction being opposite to the first rotation direction.

Generally speaking the dial-down mechanism may be implemented as a radial dial-down mechanism or as an axial dial-down mechanism. In the radial dial-down mechanism the dial-down key or keys are arranged to move in the radial direction of the mechanism. This may also be the radial direction of the injection device. In the axial dial-down mechanism, the dial-down key or keys are arranged to move in the axial direction of the injection device.

Also it should be noted that the dial-up key or keys, and the dial-down key or keys may be different keys—i.e. physically separated keys. However, it may also be that the dial-up and dial-down key is constituted by the same key. Thus, it may be that the mechanism according to the present invention comprises only a single key which is used for both dial-up and dial down.

The dial-up and dial-down cams may be arranged as openings or indentations in an outer surface part of a disc-shaped cam member. The cam member may, alternatively, also be shaped as a substantially cylindrical member. In particular, the dial-up and dial-down cams may be arranged in a substantially plane surface part of the cam member. This substantially plane surface part may be substantially perpendicular to an axial direction of the disc or cylindrical shaped cam member. The cam member may be a hollow construction, or alternatively, the cam member may be a solid construction.

In both the radial and the axial mechanism, the dial-up cam may form a curved track, such as part of a circular, elliptical or parabolic track. The dial-down cam may form part of a V-shaped track, or alternative, it may have a rectangular shape.

The dial-down mechanism may comprise a first and a second dial-up cam. Furthermore, the dial-down mechanism may comprise a first and a second dial-up key, wherein the first dial-up key may be adapted to engage and cooperate with the first dial-up cam, and wherein the second dial-up key may be adapted to engage and cooperate with the second dial-up cam.

The dial-down mechanism may further comprise a first and a second dial-down cam, and a first and a second dial-down key. The first dial-down key may be adapted to engage and cooperate with the first dial-down cam, whereas the second dial-down key may be adapted to engage and cooperate with the second dial-down cam.

It may also be that the dial-up and dial-down cams form part of regions of the same track. Furthermore, the dial-up and dial-down keys may be constituted by the same key, said key being adapted to engage and cooperate with dial-up and dial-down cams of the same track.

In the axial mechanism, the dial-up and dial-down cams may be arranged as cams having an axial component parallel to an axial direction of the injection device. The dial-up and dial-down cams may be arranged on an outer and curved surface part of a substantially cylindrical cam member. This substantially cylindrical cam member may be the dose setting member of the injection device, or it may be a separate component cooperating with the dose setting member of the injection device.

In the axial mechanism, the dial-up cam may be substantially parallel to an axial direction of the injection device. In order to be able to release an associated ratchet from a toothing the dial-down cam may form an angle, such as around 45 degrees, to the dial-up cam.

In a second aspect, the present invention relates to an axially arranged dial-down mechanism for an injection device, the dial-down mechanism comprising a rotatable member adapted to be rotated when a dose to be injected from the injection device is set, the rotatable member comprising a dial-up cam and a dial-down cam, wherein the dial-up cam is adapted to receive and engage with a key of a ratchet of the injection device during dose setting during dial-up, and wherein the dial-down cam is adapted to receive and engage with the key during dial-down, wherein the dial-up cam is substantially parallel to an axial direction of the injection device.

In this second aspect of the present invention the dial-up and dial-down cams may form part of regions of the same track. The dial-up and dial-down keys may be constituted by the same key, said key being adapted to engage and cooperate with dial-up and dial-down cams of the same track.

In a third aspect, the present invention relates to a medication delivery device, such as a handheld medication delivery device, comprising a dial-down mechanism according to the first aspect of the present invention.

BRIEF DESCRIPTION OF THE DRAWINGS

The present invention will now be described in further details with reference to the accompanying figures, wherein FIG. 1 shows the principle of a radial dial-up and dial-down mechanism where the keys on the flexible arm are used for both dial-up and dial-down,

[FIG. 2 shows] *FIGS. 2A and 2B show* a radial dial-up/dial down mechanism with separate keys for dial-up and dial-down, *where FIG. 2A shows torsion spring 18 and disc 14 over ratchet 13 (not labeled) and adjacent to nut 10 (not labeled), and FIG. 2B also shows ratchet 13 adjacent nut 10.*

FIG. 3 shows a radial dial-up/dial down mechanism with separate keys for dial-up and dial-down where the movements of the dial-down key is determined by a track in the nut, FIG. 4 shows an injection device having an integrated radial dial-down mechanism, and

[FIG. 5 shows] *FIGS. 5A and 5B show* an injection device having an integrated axial dial-down mechanism, *where FIG. 5A shows a cross-section of an injection device, and FIG. 5B shows a partial front or side elevation view of the same injection device.*

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

The dial-down mechanism according to the present invention may be implemented as an axial or a radial mechanism. Both of these mechanisms may be integrated into an injection device, such as an injection pen.

A radial solution is shown in FIG. 1. FIG. 1a shows a rotatable inner part 2 biased against a fixed outer part 1. The biasing force is provided by a torsion spring (not shown) in the counter-clockwise direction. The inner part 2, which is rotatable around a center axis 6, has one or more flexible arms 3 adapted to engage with the edges 5 in the fixed outer part 1. FIG. 1b shows the arrangement of FIG. 1a with a rotatable disc 7 (hatched region) placed on top of the inner part 2 and outer part 1. The disc 7 has an opening 8. The edges defining the opening 8 constitute dial-up and dial-down cams. A pick-up key 4 attached to, or integrated with, the flexible arm 3 operates as a cam follower when the disc 7 is rotated relative to the outer part 1.

The system illustrated in FIG. 1 is operated in the following manner:

When a dose is to be set (dial-up), the inner part 2 is rotated in the clockwise direction whereby the flexible arm 3 will move from one edge 5 to the neighboring edge or edges—depending on the angle of rotation. The inner part 2 is driven by disc 7—thus, when disc 7 is rotated the inner part 2 rotates with it. During rotation in the clockwise direction, the pick-up key 4 moves in and out along the radial direction.

When the disc 7 is rotated in the counter clockwise direction (dial-down direction) the pick-up key 4, and thereby the flexible arm 3, is lifted out of its engaging position with the edge 5 of the outer part 1. When the arm 3 is fully disengaged from the edge 5 the inner part 2 may be rotated in the counter clockwise direction relative to the outer part 1. It is a characteristic of the system shown in FIG. 1 that the pick-up key 4 is used for both dial-up (increasing a dose) and dial-down (resetting or reducing a dose).

It should be noted that the directions of rotation could be reversed so that dial-up is achieved by rotating the inner portion 2 in the counter clockwise direction. In such a configuration dial-down could be achieved by rotating disc 7 in the clockwise direction.

[FIG. 2 shows] *FIGS. 2A and 2B show* an exploded drawing of the radial embodiment of the dial-down mechanism according to the present invention. The main difference compared to the embodiment shown in FIG. 1 is that the embodiment of [FIG. 2] *FIGS. 2A and 2B* applies different pick-up keys for dial-up (pick-up key 11) and dial-down (pick-up key 12). The dial-up key 11 engages with track 15 of the disc 14, whereas dial-down key 12 engages with track 16 of the disc 14. Tracks 15 and 16 are formed as through-going openings or indentations in a planar surface of the disc 14. The dial-up tracks 15 take the form of curved tracks whereas the dial-down tracks 16 are V-shaped. An obvious alternative to the V-shape is a rectangular shape. It should be noted that the general idea is that the dial-up tracks 15 should be capable of transferring a momentum to a torsion spring 18. In the same manner, the dial-down tracks 16 should be capable of releasing the dial-down keys (and thereby release energy) in case the disc 14 is rotated just a few degrees relative to the nut 10.

The dial-down keys 12 are integrated with the flexible arms 19. These arms are fabricated of a resilient material such as for example plastic. The flexible arms 19 with integrated dial-down keys 12 form an integral part of the ratchet 13. Thus, the ratchet including arms and dial-down keys may preferably be fabricated of the same material, such as of plastic. In order to bias the dial-down keys 12 against the teeth 20 of the nut 10 a torsion spring 18 is arranged coaxially with the ratchet 13. An opening 21 is provided in the center part of the nut 10. The side wall of this opening is provided with threads 22 which are adapted to engage with a threaded outer surface of a piston rod (not shown).

FIG. 3 shows another radial embodiment according to the present invention. In this embodiment, the movement of the arm 26 is controlled by a track 23 in the nut 27. The track 23 is engaged by the track/cam follower 24 which precisely guides the dial-down key 28 from one tooth to the neighboring tooth during dial-down. In contrast to FIG. 2 the opening 25 in the center of the nut 27 is provided with a track follower 29. This track follower is adapted to engage with a track in the outer surface of a piston rod (not shown).

FIG. 4 shows an injection device having a radial dial-down mechanism according to the present invention. Among other components the injection device shown in FIG. 4 shows a dose setting member 30, a piston rod 31 having a threaded outer surface and a drive track arranged in the axial direction of the piston rod, a nut 32, a torsion spring 35, a drive member 33, the threaded portion 34 of the housing, a lease mechanism 36, a toothing mechanism 37, and ratchet 38.

A dose is set by rotating the dose setting member 30 and the nut 32 whereby the torsion spring 35 is strained. The dose setting member 30 is prevented from returning to its initial position due the toothing mechanism 37 positioned between the nut 32 and the drive member 33. In case the user wants to reduce a preset dose, the dose setting member 30 is simply rotated in the opposite direction. The interaction between ratchet 38 and nut 32 during dial-down is described in connection with FIG. 2.

[FIG. 5 shows] *FIGS. 5A and 5B show* an injection device having an axial dial-down mechanism according to the present invention. Among other components the injection device shown in FIG. [5] *5B* comprising a dose setting member 40, an opening 41 defining dial-up and dial-down cam surfaces, a cam follower 42, a torsion spring 43, a ratchet 44, and a piston rod 45. The general idea behind the axial dial-down mechanism is to use the torsion spring 43 to both drive and rotate the piston rod 45 and to ensure that the upper and lower parts of the toothing 48 remain together.

When a dose is to be set, the cam follower 42 engages with cam surface 46. As a result the torsion spring 43 is strained because the ratchet 44 is prevented from reversing due to the toothing 48. During dial-up the ratchet 44 will move up and down along cam surface 46 as the upper and lower parts of the toothing 48 rotate relative to each other. In case of dial-down the cam surface 47 will lift and thereby release the upper part of the toothing from the lower part of the toothing thereby the ratchet 44 is allowed to rotate an angle corresponding to one tooth.

The invention clamed is:

1. A dial-down mechanism for an injection device comprising a torsion spring (18) for assisting injection of a dose of medicament from the injection device, the dial-down mechanism comprising dial-up cam (15) arranged to receive and engage with a dial-up key (11), wherein the dial-up cam (15) and the dial-up key (11) are adapted to, upon rotation of a dose setting member in a first direction, cooperate to strain the torsion spring (18) of the injection device, and a dial-down cam (16) arranged to receive and engage with a dial-down key (12), wherein the dial-down cam (16) and the dial-down key (12) are adapted to, upon rotation of the dose setting member in a second direction, cooperate to release the torsion spring (18) of the injection device, the second rotation direction being opposite to the first rotation direction, wherein the dial-up and dial-down cams form part of regions of the same track, further comprising an arm wherein the dial-up and dial-down keys are both located on the same arm, said keys being adapted to engage and cooperate with dial-up and dial-down cams of the same track.

2. A dial-down mechanism according to claim 1, wherein the dial-up cam (15) forms part of a curved track.

3. A dial-down mechanism according to claim 2, wherein the curved dial-up cam (15) forms part of a circular, elliptical or parabolic track.

4. A dial-down mechanism according to claim 1 comprising a first and a second dial-up cam.

5. A dial-down mechanism according to claim 4 comprising a first and a second dial-up key, wherein the first dial-up key is adapted to engage and cooperate with the first dial-up cam, and wherein the second dial-up key is adapted to engage and cooperate with the second dial-up cam.

6. A dial-down mechanism according to claim 1, wherein the dial-down cam (16) forms part of a V-shaped track.

7. A dial-down mechanism according to claim 1 comprising a first and a second dial-down cam.

8. A dial-down mechanism according to claim 7 comprising a first and a second dial-down key, wherein the first dial-down key is adapted to engage and cooperate with the first dial-down cam, and wherein the second dial-down key is adapted to engage and cooperate with the second dial-down cam.

9. A medication delivery device comprising a dial-down mechanism according to claim 1.

10. A medication delivery device according to claim 9, wherein the medication delivery device is a handheld medication injection pen.

*11. A method for using a wind up injection pen, the method comprising the steps of*

*rotating a first element in a first direction, the direction being a dial up direction;*

*causing a second element to be rotated in the same direction as the first element;*

*straining a torsional spring;*

*moving an arm that is in engagement with one edge to a neighboring edge, wherein when the arm is engaged with an edge it prevents the torsional spring from unwinding;*

*rotating the first element in a second direction opposite the first direction;*

*moving a pick-up key and radially lifting the arm out of engagement with an edge and when the arm is fully disengaged from an edge allowing the second rotatable element to rotate in the second direction and allowing the strain on the spring to be decreased.*

* * * * *